US012721546B2

(12) United States Patent
Wang et al.

(10) Patent No.: US 12,721,546 B2
(45) Date of Patent: Sep. 1, 2026

(54) FOOTWEAR SENSORS FOR HUMAN MOVEMENT MEASUREMENT

(71) Applicant: Universiteit Twente, Enschede (NL)

(72) Inventors: Huawei Wang, Enschede (NL); Massimo Sartori, Enschede (NL)

(73) Assignee: Universiteit Twente, Enschede (NL)

(*) Notice: Subject to any disclaimer, the term of this patent is extended or adjusted under 35 U.S.C. 154(b) by 473 days.

(21) Appl. No.: 18/265,698

(22) PCT Filed: Dec. 13, 2021

(86) PCT No.: PCT/EP2021/085396
§ 371 (c)(1),
(2) Date: Jun. 7, 2023

(87) PCT Pub. No.: WO2022/128866
PCT Pub. Date: Jun. 23, 2022

(65) Prior Publication Data
US 2024/0032822 A1 Feb. 1, 2024

Related U.S. Application Data

(60) Provisional application No. 63/124,940, filed on Dec. 14, 2020.

(51) Int. Cl.
*A61B 5/11* (2006.01)
*A43B 3/40* (2022.01)
(Continued)

(52) U.S. Cl.
CPC .............. *A61B 5/1116* (2013.01); *A43B 3/40* (2022.01); *A43B 3/44* (2022.01); *A61B 5/0077* (2013.01);
(Continued)

(58) Field of Classification Search
CPC ... A61B 5/1116; A61B 5/0077; A61B 5/1038; A61B 5/112; A61B 5/6807;
(Continued)

(56) References Cited

U.S. PATENT DOCUMENTS 9,016,961 B2 4/2015 Hulse
2012/0253234 A1* 10/2012 Yang .................... A61B 5/1038 600/595
(Continued)

FOREIGN PATENT DOCUMENTS

CN 102369046 A 3/2012
CN 106384472 A 2/2017
(Continued)

OTHER PUBLICATIONS

Paramotor Planet. (Sep. 26, 2020). Action camera foot mount. Paramotor Planet. https://web.archive.org/web/20200926233731/https://paramotorplanet.com/product/action-camera-foot-mount/ (Year: 2020).*
(Continued)

*Primary Examiner* — Adam J Eiseman
*Assistant Examiner* — Lucy Eppert
(74) *Attorney, Agent, or Firm* — J. Robin Rohlicek

(57) ABSTRACT

A system comprising a body wearable unit, with one or more cameras, a control system, and an electrical power source and a method for generating wearer data using the system, wherein the method comprises monitoring with one or more cameras a user wearing the wearable unit and providing a related camera signal; generating wearer data based on the related camera signal, wherein the wearer data comprise one or more of (i) wearer posture related data and (ii) wearer movement related data.

30 Claims, 5 Drawing Sheets

(51) Int. Cl.

| | |
|---|---|
| ***A43B 3/44*** | (2022.01) |
| ***A61B 5/00*** | (2006.01) |
| ***A61B 5/103*** | (2006.01) |

(52) U.S. Cl.

CPC ............ *A61B 5/1038* (2013.01); *A61B 5/112* (2013.01); *A61B 5/6807* (2013.01); *A61B 5/7267* (2013.01); *A61B 2560/0223* (2013.01); *A61B 2562/0219* (2013.01); *A61B 2562/0247* (2013.01)

(58) Field of Classification Search

CPC .......... A61B 5/7267; A61B 2560/0223; A61B 2562/0219; A61B 2562/0247; A61B 2505/09; A61B 5/0022; A61B 5/224; A61B 5/4561; A43B 3/40; A43B 3/44; A43B 3/46; A43B 3/48

See application file for complete search history.

(56) References Cited

U.S. PATENT DOCUMENTS

| | | | | |
|---|---|---|---|---|
| 2018/0132758 | A1* | 5/2018 | Benford | A61B 5/1038 |
| 2019/0234817 | A1* | 8/2019 | Sun | A61B 5/0536 |
| 2020/0000373 | A1 | 1/2020 | Agrawal et al. | |
| 2021/0068492 | A1* | 3/2021 | Onyekachi | A43B 1/0054 |
| 2021/0174908 | A1* | 6/2021 | Benjamin | C07K 16/2818 |
| 2021/0236020 | A1* | 8/2021 | Matijevich | A61B 5/1038 |
| 2021/0378565 | A1* | 12/2021 | Kettel | A61L 15/56 |
| 2022/0257146 | A1* | 8/2022 | Anderson | G01S 13/08 |
| 2024/0032822 | A1* | 2/2024 | Wang | A61B 5/112 |
| 2024/0115159 | A1* | 4/2024 | Segal | A61B 5/4848 |

FOREIGN PATENT DOCUMENTS

| | | | |
|---|---|---|---|
| CN | 107223247 | A | 9/2017 |
| CN | 211022692 | U | 7/2020 |
| CN | 111632353 | A | 9/2020 |
| WO | 2007130287 | A2 | 11/2007 |
| WO | 2019213012 | | 11/2019 |

OTHER PUBLICATIONS

Siddiqui, M. Zulqarnain, et al. "Advanced Mechanism to Empower Blind and Visually-Impaired." International Journal of Computer Science and Mobile Computing, vol. 8, No. 12, Dec. 2019, pp. 10-17, https://ijcsmc.com/docs/papers/December2019/V8I12201904.pdf.

International Search Report and Written Opinion, PCT Application No. PCT/EP2021/085396, mailed Apr. 7, 2022 (10 pages).

Kemp, Charles & Fitzpatrick, Paul. (2004). "Shoes as a Platform for Vision" MIT Computer Science and Artificial Intelligence Laboratory.

Fitzpatrick, Paul & Kemp, Charles. (2004). Shoes as a Platform for Vision. Massachusetts Institute of Technology, Computer Science and Artificial Intelligence Laboratory.

Pugh, Jena & Mateo, Alex. "How to strap a gopro to your shoe and ride a roller coaster." (Aug. 15, 2014). Bestoforlando.com.

Sunarya, Unang, et al., "Feature Analysis of Smart Shoe Sensors for Classification of Gait Patters." (Nov. 3, 2020) Senors, 20, 6253, mdpi.com/journal/sensors. doi:10.3390/s20216253.

Third Party Observations in EP Application No. EP4258988. issued Apr. 23, 2024 (3 pages).

Office Action, Chinese Application No. 202180082445.7, mailed Sep. 26, 2025 (11 pages).

Office Action, Chinese Application No. 202180082445.7, mailed May 6, 2026 (10 pages).

* cited by examiner

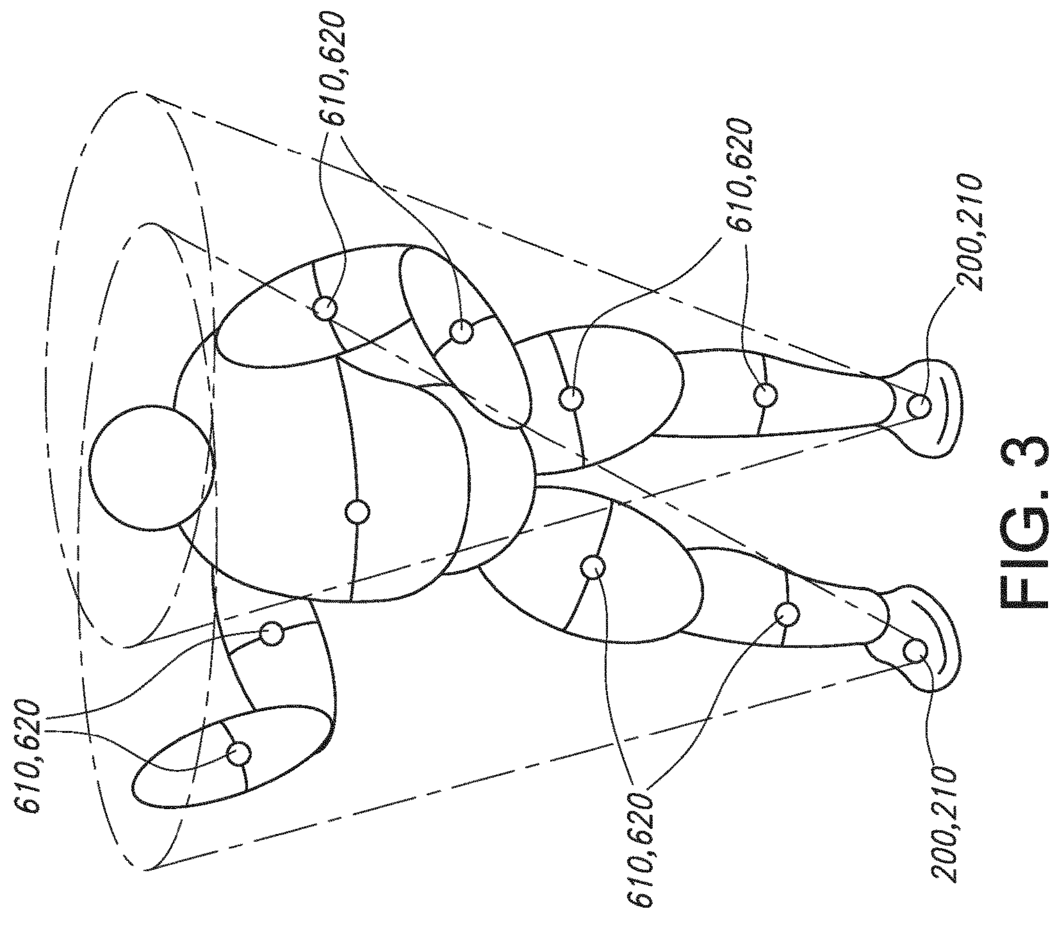
FIG. 3
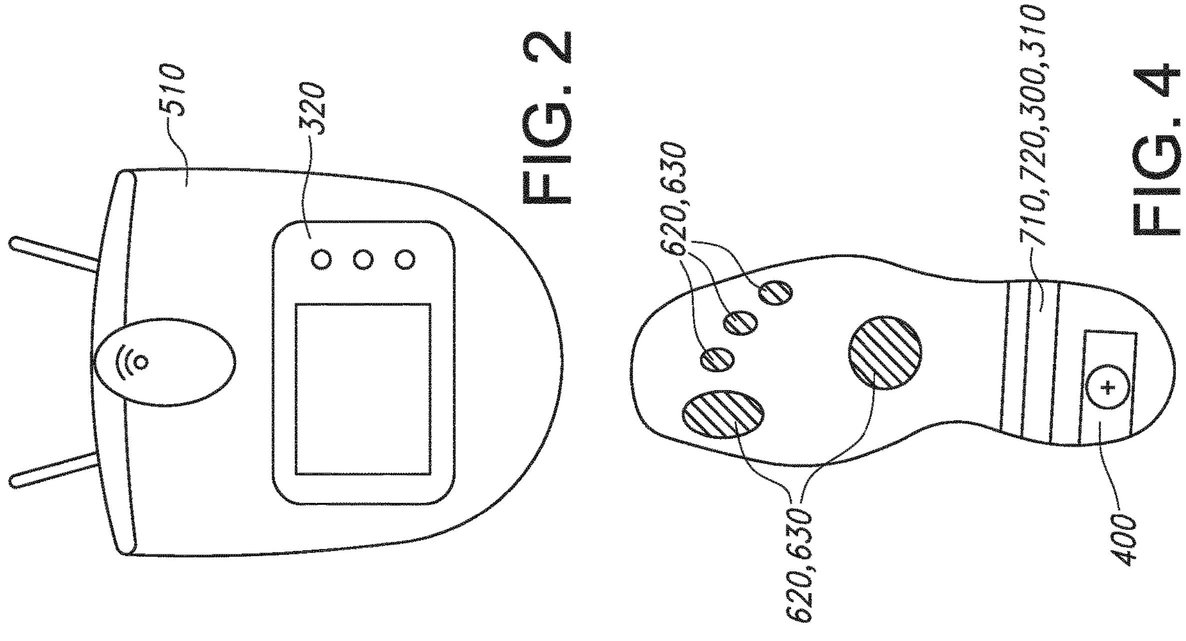
FIG. 2
FIG. 4

FOOTWEAR SENSORS FOR HUMAN MOVEMENT MEASUREMENT

CROSS REFERENCE TO RELATED APPLICATIONS

This application is a 371 national stage application of International Application No. PCT/EP2021/085396, filed Dec. 13, 2021, which claims the benefit of the filing date of U.S. Provisional Application No. 63/124,940, filed Dec. 14, 2020, the contents of which are hereby incorporated by reference in their entireties.

FIELD OF THE INVENTION

The invention relates to a system comprising a body wearable unit, such as footwear. The invention further relates to method for generating e.g. posture and/or movement data using such system. The invention further relates to a kit of parts comprising the body wearable unit.

BACKGROUND OF THE INVENTION

Body wearable systems used to record information about the posture and movement of the wearer are known in the art. U.S. Ser. No. 10/783,376, for instance, describes an information processing apparatus which includes a processor which executes a video data acquisition process of acquiring data on a video of at least one moving object as video data; a measurement information data acquisition process of acquiring data representing measurement information on the object as measurement information data; an object specifying process of specifying the object corresponding to the measurement information data included in the video, as an analysis target; a color specifying process of specifying a color of the analysis target as an object color; and a determination process of determining the object color specified by the color specifying process as a display color to be displayed when the measurement information data is displayed.

SUMMARY OF THE INVENTION

Quantitative estimation of the body movement information, for example body posture, may be fundamental for many fields, such as healthcare, sports, and entertainment among others.

A vital part in the development of sports medicine and related physical therapy may include an accurate estimation of the physical condition of an athlete while an activity or exercise is performed. This may include understanding quantitatively the extent of the forces and torques exerted on the limbs, joints, and muscles of an athlete. To avoid damage to the muscle tissue, tendons and ligaments during an activity or exercise, the athlete may need to maintain good form. In many situations, it may not be possible for athletes to determine this simply by observation. This is especially true for muscle force as it is not possible to measure this any direct manner. Further, physical trainers and coaches may rely on human observation to assess the form of an athlete in the course of an exercise or activity. A possible limitation to this is that physical therapists may lack quantitative information vital to treating neuromuscular diseases or sports related injuries. Moreover, amateur sports enthusiasts may lack the means to assess the quality of performance of their own sport or activity due to the lack of access to trained supervision. Information such as muscle usage and force generated are sorely lacking especially for sporting enthusiasts to improve their endurance or strength. Additionally, easily accessible focused training feedback that is personalized to a user is unavailable, such as daily feedback for someone training to run a marathon.

Further, consumers may lack a means of assessing their individual physical condition during everyday activities. With an increase in awareness about personal well-being, an average consumer lacks the tools to objectively gauge the impact of their daily routine on their muscles and joints. They appear to lack portable and non-intrusive tools to consistently catalogue the impact of daily activities on their body over prolonged periods of time. Besides the requirements to quantitatively measure body motions, another critical feature that may be needed is the wearability, where the measurement system may be able to follow users to almost any place, while not restricting freedom of movement.

In the development of prosthetics, it may be difficult to adjust and tune the operation of a prosthetic such as an artificial limb to a specific user. This may particularly be the case due to the vast differences in physical characteristics of individuals. Lacking quantitative information about these parameters, for example the gait of a person, may limit the application of the prosthetic and negatively impact the quality of life of the person suffering from such a condition. This may particularly be important for the elderly who may suffer from the acute risk of falling.

In the entertainment industry, quantitative motion capture technology may be paramount to animating computer generated avatars, augmented reality applications, and visual effects applications, to the manually tuned motions by the animators. Further, conventional optical motion capture techniques use several cameras placed in the vicinity of the actor to track their motion, by means of highlighted targets on the body of an actor. This may pose many disadvantages such as expensive equipment that utilizes many cameras, lack of maneuverability of the actor, restrictions to indoor locations, complicated calibration software, etc. It is an expensive and complicated challenge to render and animate a digital avatar using existing motion capture technology.

Hence, it is an aspect of the invention to provide (kinematic) information related to the posture and/or movement of an individual during an activity or exercise using a body wearable unit, which preferably further at least partly obviates one or more of above-described drawbacks. The present invention may have as object to overcome or ameliorate at least one of the disadvantages of the prior art, or to provide a useful alternative.

According to a first aspect, the invention provides a system which may comprise a body wearable unit ("body wearable", "wearable", "wearable unit"), one or more cameras, a control system, and an electrical power source. The body wearable unit may comprise the one or more cameras, the control system, and the electrical power source. The one or more cameras may be configured to monitor a user wearing the body wearable unit and to provide a related camera signal. The electrical power source may be configured to provide electrical power to the one or more cameras, and the control system. The control system may be configured to generate wearer data based on the related camera signal. The wearer data may comprise one or more of (i) wearer posture related data and (ii) wearer movement related data. The body wearable unit may especially comprise footwear and the one or more cameras, the control system, and the electrical power source that are functionally coupled to the body wearable unit. Hence, in specific embodiments the invention provides a system 1 comprising a body wearable unit, one or more cameras, a control system, and an electrical power source; wherein: (A) the body wearable unit comprises the one or more cameras, the control system, and the electrical power source; (B) the one or more cameras are configured to monitor a user wearing the wearable unit and to provide a related camera signal; (C) the electrical power source is configured to provide electrical power to the one or more cameras, and the control system; (D) the control system is configured to generate wearer data based on the related camera signal; wherein the wearer data comprise one or more of (i) wearer posture related data and (ii) wearer movement related data; (E) the body wearable unit comprises footwear; and (F) the one or more cameras, the control system, and the electrical power source are functionally coupled to the body wearable unit. Further, in an aspect the invention provides a wearable (kinetic) data measure system comprising a (pair) of shoe(s) or footwear(s) with at least one camera including an optical or a thermal or a radar or a depth camera, with or without pressure sensors to detect stepping forces, with or without a inertial measure unit (IMU) or satellite based navigation systems to measure global location, with machine learning technology to extract human postures from camera images, with optimal trajectory simulation or machine learning technology to extract sensor data, and process said sensor data to obtain kinetic information such as joint torques and muscle states.

Especially, with such a system it may be possible to measure information about the posture, or movement, or a combination thereof with relative ease. Further, with such a system it may be relatively easy to train a body wearable unit for/by a specific user. The body wearable unit may be pre-trained, and may be further trained in a shop, at home, at a sport field, in a sport lab, etc.

In embodiments, the body wearable unit may be footwear for example a sports shoe which may comprise a camera, a control system, and an electrical power source. In embodiments, the body wearable unit may be a glove, or a band that may be secured to any limb, or appendage, or segment of the body; or a helmet, a sports suit (like a swimming suit), a life jacket, a vest, a sports harness (like for kite surfing, wind surfing), a body protector, etc. Hence, the term "user" herein especially refers to a human (wearing the body wearable unit).

Especially, the invention is defined in relation to footwear as an embodiments of a body wearable unit. Footwear may include boots, shoes, sandals, slipper, socks, etc. Footwear may also further include sport specific footwear such as soccer shoes, running shoes, flippers, and skates. Especially, the footwear may comprise a shoe or a boot, more especially a shoe (such as a sports shoe).

Optionally, footwear may also comprise ski boots, snowboard boots, langlauf boots. In specific embodiments, the body wearable may comprise a ski, a langlauf ski, and a snowboard.

In embodiments the camera may be secured to the front of footwear, for example on the front side of the shoe, and directed upwards towards the body of the wearer, to generate wearer data related to movement and posture from the front side or anterior of the wearer. In this embodiment, the camera may have a field of view which encompasses a substantial part of the front of the wearer's body.

In embodiments, the body wearable unit may comprise two cameras, where the second camera is attached to the back of the shoe. The second camera may be directed at the posterior of the body of the wearer and provides wearer data related to the position and movement of the wearer during an activity or exercise from the rear side or posterior of the wearer.

In embodiments the body wearable unit may comprise more than two cameras, such as (strategically) placed on the footwear. Especially, the camera may record image data related to the posture and movement of the wearer from a multitude of directions to augment the image data from one or more other cameras on the body wearable unit.

In embodiments, a pair of footwear may include one or more cameras on the front side of either shoe to provide binocular vision. In further embodiments, the pair of footwear may include one or more cameras on the front and back side of either shoe, which may further extend the field of view and/or allow a more reliable and/or complete generation of wearer data.

In embodiments, the one or more cameras may record image data to provide a related camera signal, which may be directed as a data stream to the control system. The control system may process the image data to generate wearer data. Further, the control system may control the operation of the cameras, which comprises adjusting the parameters at which image data is recorded such as shutter speed, exposure, frame rate, resolution, image stabilization, focus, aperture, and ISO settings. The control system may further direct the camera signal either to be processed within the control system in the body wearable unit or to an external receiver, in which case the wearer data is processed externally. The camera and the control system may both be powered by the electrical power source. The related camera signal may comprise data generated during monitoring the user, such as one or more images.

In embodiments, the one or more cameras and the control system may be electrically connected to the power source. The control system determines the distribution of electrical power to the control system, and the one or more cameras. In embodiments, the system may comprise a control system which may be electrically connected to the components in the system. This may include the physical connections or wires required to transfer power to the different components and may further include the cables for the transfer of the data between the different components. The body wearable unit may comprise pathways for wires stitched within the footwear. In further embodiments, the electrical wires may be bonded on the outside of the footwear.

In embodiments, the electrical power source may be configured to provide a potential difference in the range of 1V-12V. The control system may regulate and control the operation of different components in the system.

In embodiments, one or more of the one or more cameras, especially all of the one or more cameras, may have a frame rate of at least frames per second, such as at least q00 frames per second, like in specific embodiments 240 frames per second. Further, in embodiments one or more of the one or more cameras, especially all of the one or more cameras, have a resolution of at least 1280×720 pixels. Hence, in embodiments, the one or more cameras may possess a framerate of at least frames per second to provide sufficient number of image samples to resolve movement related information. In embodiments, the one or more cameras may have a resolution of at least 1280×720 pixels to capture image data with sufficient detail to infer posture related information.

Posture related information may comprise images of the limbs or segments of the wearer's body from which the contours of limbs, location of joints and orientation of limbs may be inferred. Movement related information may comprise a series of images of the limbs of the wearer from which the motion of limbs around one or more joints may be inferred. Movement related information may further comprise a series of images of the torso or other segments of the wearer's body from which additional information such twisting of the torso, bending at the hips, or craning of the neck may be inferred.

Posture may be defined as the attitude assumed by the body either with support during the course of muscular activity, or as a result of the coordinated action performed by a group of muscles working to maintain the stability.

Dynamic posture may refer to how a person holds himself/herself when moving, like when walking, running, or bending over to pick up something. It is usually required to form an efficient basis for movement. Muscles and non-contractile structures may have to work to adapt to changing circumstances.

Static posture is how a person holds himself/herself when not moving, like when sitting, standing, or sleeping. Body segments are aligned and maintained in fixed positions. This is usually achieved by co-ordination and interaction of various muscle groups which are working statically to counteract gravity and other forces.

Herein, the term "posture", and similar terms, may especially refer to static posture. Herein the term "movement", and similar terms, may especially refer to dynamic posture.

The term "posture related data" may refer to posture data, like images, but may also refer to processed data, like a conclusion on a specific posture like "standing", "sitting", "sleeping", "straight", "bent", "dropped shoulder", "instable static position", etc. etc. Such conclusion may also be indicated by values.

The term "movement related data" may refer to movement data, like a plurality of images over time, like a movie, but may also refer to processed data, like a conclusion on a specific movement like "walking", "running", "swimming", "shambling", "instable dynamic behavior", etc. etc. Such conclusion may also be indicated by values.

Posture and/or movement related data may also include a speed value, a force value, a torque value, etc.

In embodiments, one or more of the cameras may be selected from the group of an optical camera, an infrared camera, a multispectral camera, and a LIDAR sensor.

The camera may (thus) not be limited to optical cameras and may also comprise other image recording systems. In embodiments, infrared cameras may be particularly preferable for recording information at night or in unfavorable lighting conditions. Alternatively or additionally, local heat information of the body of the wearer may be determined. In embodiments, multispectral cameras may be used to record mid-wave infrared and long-wave infrared imaging, which extends the utility of the system by measuring radiation that's inherent to an object, regardless of the presence of any external light source, hence ideal in poor lighting conditions. In further embodiments, LIDAR may be used, which uses rapidly fired lasers to determine position and movement information with high accuracy, which also functions well in poor lighting conditions. In further embodiments, the system may also use a combination of the devices mentioned before to augment the generated wearer data with image data comprising of a wide spectrum of wavelengths.

The system may be powered electronically by means of an electrical power source. This may include the supply of power to the different components used in the device. In embodiments, the power source may be a portable power source to be used and may be attached to the body wearable unit. This may include single use batteries of the type comprising Zinc Carbon, Magnesium (Mg/MnO2), Mercury (Zn/HgO), Alkaline (Zn/Alkaline/MnO2), Silver/Zinc (Zn/Ag2O), Lithium/Soluble Cathode, Lithium/Solid Cathode, and Lithium/Solid Electrolyte. In further embodiments, the power supply may include rechargeable batteries of the type comprising Lead-Acid Batteries, Nickel-Cadmium Batteries, Nickel-Metal Hydride Batteries, Lithium-Ion Batteries.

In embodiments, the system may be charged wirelessly using charging pads that use tightly-coupled electromagnetic inductive or non-radiative charging. In further embodiments, charging bowls or through-surface type chargers may be used that facilitate loosely-coupled or radiative electromagnetic resonant charging, especially for charging up to a few centimeters away. In yet further embodiments, uncoupled radio frequency wireless charging may be used that allows charging at distances of many feet. In other embodiments, the system may be wirelessly charged using piezoelectric sensors, which may generate a voltage from footstep impact. These embodiments allow the unrestricted movement of the user during an activity or exercise. In other embodiments, the power supply may be wired, where the power supply unit draws power from an external source by means wires that can be plugged into an external power source. In yet further embodiments, the electrical power source may draw power from a combination of wired and wireless sources. Hence, in embodiments the electrical power source of the body wearable unit, especially the footwear, may be charged wired or wireless. For instance, the body wearable unit, especially the footwear, may comprise a port, like a USB port, for wired charging. However, charging may also be wireless.

In embodiments, the body wearable unit may comprise additional sensors. In these embodiments, the control system may be configured to control the operation of these other sensors. Recorded signals may include image data from the camera(s) from related camera signal(s) and related sensor signal(s) from one or more sensors.

In embodiments, the one or more cameras may record the body of the wearer looking upwards from a lower extremity. The recorded position data may comprise images which are used to identify the position of the limbs and the body of the wearer in relation to each other. Further the recorded movement data may comprise a sequence of images captured by the one or more cameras to identify the relative linear and angular velocities of the different limbs identified in the position data.

In embodiments, two cameras on either footwear may be used in tandem to provide binocular vision.

In embodiments, the control system may process the related sensor and camera signals locally to generate wearer data. In embodiments, the control system may provide the related camera and sensor signals to a communication system, for further external processing. In further embodiments, the control system may provide processed wearer data to the communication system, to be transmitted to external devices.

In embodiments, the cameras, the power supply, and the control system may be attached to a body wearable unit. Further, these components may be secured or attached to the footwear or placed within cavities in the footwear or a combination thereof.

In embodiments, the body wearable unit may further comprise a communication system and the electrical power source may be configured to provide electrical power to the communication system. Further, the communication system may be functionally coupled to body wearable unit, especially the footwear. In embodiments, a sole part of the footwear may comprise the communication system.

In embodiments, the communication system may be electrically powered by the electrical power source. In further embodiments, the communication system may be connected to the control system by means of cables, to facilitate communication with the control system. In embodiments, the control system may provide related image data from one or more cameras to the communication system. In embodiments, position information from one or more sensors may also be provided to the communication system. In embodiments, where sensors record movement information, the movement information may also be provided to the communication system. In embodiments, where sensor signals from sensors are transmitted wirelessly, the communication system may be configured to provide said signals to the control system. In embodiments, the communication system may be configured to provide a continuous stream of data from related camera signal or sensor signals or a combination thereof.

In embodiments, the communication system may facilitate communication between the local control system comprised by the footwear to an external remote communication system. This facilitates the alteration of the mode of operation of the system at any point before, during or after an activity or exercise. In further embodiments, the communication system may be configured to transmit the wearer data, or the related sensor or camera signals, or a combination thereof to an external receiver. This provides the benefit of processing the data externally, or visualizing the data on a computer or mobile device, or storing the data on an external centralized database. Hence, in specific embodiments the control system may comprise a local control system, comprised by the body wearable unit, such as a sole part of footwear, and a remote control system, configured external of the body wearable unit, such as a sole part of footwear.

In embodiments, the communication system may comprise a storage device, such as to record wearer data over the course of an exercise or activity. The stored wearer data may then be extracted from the communication system for further analysis post the exercise or activity. In embodiments, the storage device may comprise a flash memory device chosen from the group of a CompactFlash, a PCMCIA, a secure digital card, a multimedia card, or a memory stick, etc. In further embodiments, the communication system may comprise a port from the group of a PS/02, a serial port, a parallel port, an ethernet port, or an USB Port. The port described in this embodiment may be used to access stored wearer data in the communication system. In further embodiments, the port may also be used to configure a different mode of operation of the body wearable unit or a specific parameter of a camera or a sensor.

In embodiments, the communication system may be configured for the transmission of wearer data by means of wireless technology selected from the group of Wi-Fi, cellular internet: 3G, 4G & 5G, Zigbee, Z-Wave, Li-Fi, V2X, LPWA, Bluetooth, radio waves and infrared waves.

In embodiments, the communication system may transfer wearer data to an external receiver by means of wireless technology. Wireless transmission of data allows the wearer data to be accessible real-time during the course of an exercise or an activity. In embodiments, the transfer of wearer data may occur over a Wi-Fi network. Wi-Fi is a family of wireless network protocols, based on the IEEE 802.11 family of standards, which facilitates local area networking, allowing communication system to exchange data by radio waves. In further embodiments, the communication system may use broadband cellular technology such as 4G or 5G which allow transport of multiple signals at a wide range of frequencies and enables multiple messages to be sent simultaneously. In yet further embodiments, the communication system may use Bluetooth, which is a short-range wireless technology standard that is useful for exchanging data over short distances using high frequency radio waves from 2.402 GHz to 2.48 GHz. In further embodiments, the communication system may use any other type of wireless technology such as Zigbee, Z-Wave, Li-Fi, V2X, LPWA, radio waves and infrared waves. Fast, low latency wireless communication may provide the advantage of altering the mode of operation or the system, adjust parameters of one or more cameras or sensors to customize the type of wearer data based on real-time observation of generated wearer data.

The communication system may be configured to provide the wearer data to a receiver external of the body wearable unit.

In embodiments, the wearer data may be processed externally, thus avoiding encumbering the wearer with bulky or heavy components that may affect the activity or exercise performed. Moreover, transmissibility of wearer data in real time has the advantage of maintaining a database in real-time of a multitude of users. Thus, facilitating posture analysis of a group of users especially in synchronized exercises or activities. Additionally, external processing has the benefit of performing further detailed analysis of the wearer data, or camera signal or sensor signal or a combination thereof. This provides the advantage of performing further analysis of the information which may require significant computational resources.

The control system may comprise a local control system and a remote control system. The electrical power source may be configured to provide electrical power to the local control system which is functionally coupled to the body wearable unit, such as footwear. The communication system may be configured to communicate between the local control system and the remote control system. The control system may be configured to generate wearer data based on (i) the related camera signal and (ii) information from the remote control system.

In embodiments, the control system may comprise a local control system and a remote control system, which are connected by means of the communication system which facilitates the transfer of data and instruction to and from these systems. In embodiments, the local control system may be a part of the body wearable unit, such as attached to the footwear or contained in the footwear, like in the sole part.

The local control system may be powered by the electrical power source and may control the operation of the cameras.

In embodiments, where the system may comprise additional sensors such as pressure or inertial measure unit sensors, these sensors may be controlled by the local control system. The extent of control of the local control system may extend to extracting related sensor signals, calibration of sensors or altering their mode of operation. The sensor signals recorded by the sensors form an information stream that may be directed to the local control system. In embodiments, the wearer data may be generated or processed from one or more sensor signals or camera signals or a combination thereof, by the local control system housed in the body wearable unit. In other embodiments, the wearer data may be directed by the local control system to the communication system. In yet further embodiments, the local control system may direct a part of the one or more sensor signal or camera signal or combination thereof to the processing unit and a part to the communication system. In embodiments, the mode of operation of the control system may determine if the data is processed locally or externally. In further embodiments, the mode of operation of the local control system is determined by the remote control system. The remote control system may be used to configure the operation of the local control system, hence by extension may be used to control the cameras or one or more sensors or a combination thereof. In embodiments, the remote control system may also determine how the sensor signals or camera signals or a combination thereof are processed i.e. locally or externally. Depending on the nature and the volume of the wearer data collected, it may be advantageous to process the data externally. In embodiments, the remote control system may be a dedicated external system configured to be in communication with the local control system. In further embodiments, the remote control system may be an application executed on a computer or mobile device.

In embodiments, the body wearable unit, such as in embodiments the footwear, may comprise a port, such as a USB port, functionally coupled to the (local) control system. In such embodiments, (stored) wearer data may be conveyed to an external device via the port. Hence, in such embodiments a (wireless) communication system may not be necessary or may be an additional option.

The footwear may comprise a front part wherein the one or more cameras may comprise a first camera, wherein the first camera may be physically coupled to the front part of the footwear.

The camera secured to the front of the shoe may form the primary configuration and may be the preferred configuration when only one camera is used. A camera secured to the front of the shoe has the advantage of providing a field of view from the lower extremity encompassing the bulk of the front of the wearer and hence most of the exhibited motion of the limbs and segments of the wearer's body.

The footwear may comprise a back part, wherein the one or more cameras may comprise a second camera, wherein the second camera may be physically coupled to the back part of the footwear. This provides the advantage of generating wearer data by recording images of the posterior of the wearer over the course of the exercise or activity. The images recorded from the back may supplement the wearer data obtained from the front camera to improve posture and movement detection in applications where higher fidelity is required.

The first camera may be physically coupled to the front part of the footwear by means of one or more of (a) a shoelace, (b) a stitched cavity, (c) a Velcro strap connection, and (d) a camera holder element fastened below or between a shoelace or Velcro strap.

In embodiments, the first camera may have appendages that allow it to be hooked on to the shoelaces. In further embodiments, the shoe may have loops through which the shoelaces may be threaded. In embodiments, the shoe may be designed to house the first camera such as by using one or more layers of cross woven threads that may secure the camera in place. In embodiments, the footwear may possess a cavity stitched into the collar, upper or the tongue of the shoe. In yet further embodiments, the loop side of the Velcro may be attached or stitched onto the shoe with the hoop side attached to the back of the camera. This allows for the camera to be hitched to the shoe. The Velcro strap may further allow for multiple positions in which the camera may be secured, which may improve maneuverability of the camera. In further embodiments, a specifically designed camera holder or mount may be attached to the shoe. The camera holder may be fastened to the shoelaces or below them. In embodiments, the camera holder may also be secured to the shoe by means of Velcro straps or may be secured in place using one or more layers of cross woven threads. These embodiments allow the camera to be secured in a specific position during the execution of the exercise or activity.

The second camera may be physically coupled to the back part of the footwear by means of one or more of (a) a stitched cavity, (b) a Velcro strap connection, and (c) a camera holder element fastened below or between a Velcro strap.

The second camera may be secured to the back of the shoe which may be the heel counter, heel tab or backstay of the shoe. In embodiments, the shoe may be designed to accommodate a second camera at the back within a stitched cavity. In further embodiments, the loop part of the Velcro may be stitched or bonded to the back of the shoe and the hoop part of the Velcro may be attached to the back of the camera, allowing it to be secured to the back of the shoe. In further embodiments a camera mount may be bonded, or stitched or attached by means of Velcro, allowing for the camera to be held in a specific orientation. This is useful for specific situations where higher fidelity is required in the positioning of the camera.

In further embodiments, the one or more cameras may be attached to the textile or leather used in the footwear in a sandwich structure, where the base of the camera may be placed between two layers of textile or leather that are glued together. The top layer of the two layers may have holes to prevent occlusion of the camera lens. This provides the benefit of not using additional material, a safe housing for components and ensures that components are firmly secured within the body of the footwear. In further embodiments, power and transfer cables may be routed between the layers of textile or leather, which has the benefit of protecting the cables from accidental damage during the course of the exercise or activity, and protects the wearer by preventing direct contact with the electronics.

In yet further embodiments, the system may comprise adjustable periscope zoom lenses, which may be secured onto the one or more cameras. Image data may be provided to the camera lenses via periscope lenses which allows a camera to be installed in the footwear in a more convenient orientation not necessarily directed towards the wearer.

In embodiments, the system may comprise a body wearable unit with additional sensors, where some of the sensors may be attached or secured onto the body of the wearer external from the body wearable unit and/or some of the sensors may be comprised the body wearable unit.

In embodiments the (additional) sensors may be attached selected from a multitude of ways, such as being tied directly to the wearer by means of rope, lace or other fasteners. In embodiments, they may be secured to clothing by means of clips, hooks, or other securing links. In further embodiments, they may also be adhesively attached or stitched onto clothing. In embodiments they may be secured to plastic or cloth straps that may then be secured to the body of the wearer. In further embodiments, 3D printed objects may be used to facilitate the securing of these components at strategic locations on the body of the wearer. In further embodiments, the sensors may be stitched between layers of clothing. In yet further embodiments, the sensors may be attached to footwear externally by means of securing links or fasteners. In certain embodiments, the footwear may be specifically designed to accommodate a number of these components within the footwear. The (additional) sensors may be distributed over the body of the wearer to provide information on the position and movement of the different limbs, or segments of the wearer's body during an activity or exercise. Additional sensors may also be configured remote from the user. The additional sensors may be optional.

The footwear may comprise a sole part. In embodiments, the sole part may comprise at least part of the control system. In further embodiments, the sole part may comprise the electrical power source. The sole part may be resilient. The sole part may comprise gas cavities. The sole part may comprise an external structure for grip, such as for winter grip, city grip, traction, anti-slip, or a spike(d) sole part. The sole part may also be stiff, like in the case of ski boots.

In embodiments, the sole part may comprise the local control system. Yet, as indicated above, the sole part may comprise the communication system. Hence, one or more of the local control system, the electrical power source, and the communication system may be integrated in the sole part. Other embodiments, however, may also be possible.

In embodiments, the footwear may house the other major components such as (part of) the control system and the electrical power source. In further embodiments, the control system may be housed in the sole of the footwear. These may be embedded in cavities in the sole of the shoe that are designed to accommodate the shape of these components. This allows for these components to be secured fast, limiting the amount of movement or displacement these components may experience over the course of the exercise or activity. The rubber or polyurethane, or polyvinyl chloride (PVC) compounds used in modern footwear may help cushion these components from hard impacts when the wearer engages in an exercise or activity. In embodiments, the footwear may comprise a part of the control system i.e. the local control system. Housing, components in the sole of the footwear may provide the benefit of not hindering the user and providing comfortable use of the footwear. Further, it protects the user from direct contact with the electronics.

The system may in embodiments comprise an inertial measure unit sensor. The inertial measure unit sensor may be configured external of the body wearable unit, such as external of the footwear. In embodiments, the inertial measure unit sensor may not physically coupled to the body wearable unit, such as the footwear. However, inertial measure unit sensor may be coupled to other parts of the body (than to which the footwear is functionally coupled).

In embodiments, the system may also comprise one or more inertial sensors, which may not be limited to being placed on the footwear, rather may be intended to be distributed over the wearers body, especially on the limbs or segments of the wearer's body. The inertial measure units produce sensor signals about the position and motion of the different limbs or segments of the body. In embodiments, the generated sensor signals may be used by the control system in conjunction with the camera signals to generate wearer data. In further embodiments, the generated sensor signals may be used initially to calibrate the system. This embodiment may subsequently be used without additional sensors, where wearer data is generated solely from related camera signals.

In embodiments the system may use camera data to estimate leg posture by means of an artificial neural network to generate an analogous biomechanical digital twin of the user, from which it may be possible to subsequently estimate joint torque and muscle force.

The inertial measure unit may comprise one or more of a gyroscope, an accelerometer, and a magnetometer. In embodiments the inertial measure units may comprise a gyroscope or an accelerometer or a magnetometer or a combination thereof. The gyroscope may provide information about the changes in the orientation, which is vital to generating posture related wearer data. The magnetometer measures orientation information based on magnetic fields which may help identify orientation with a high degree of accuracy. The accelerometer measures acceleration, which when attached to a limb or appendage can generate movement, force, or torque related wearer data. In embodiments, the inertial measure unit may comprise one or more of these devices to measure the position and acceleration of the wearer's limbs during an exercise or activity. These units may further house an independent power source to provide electrical power to the inertial measure units. In embodiments, the inertial measure units may be secured onto clothing by means of hooks or pins. In further embodiments, the inertial measure units may be attached to the wearer by means of straps or belts. In further embodiments, the inertial measure units may be in communication with the control system which directs the mode of their operation.

The optional pressure insole may comprise one or more pressure sensors. In specific embodiments, the pressure insole may be physically coupled to the body wearable unit. For instance, the pressure insole may be contained by the footwear. Hence, in embodiments the footwear may further comprise the pressure insole, wherein the pressure insole may be functionally coupled to the body wearable unit, wherein the electrical power source may be configured to provide electrical power to the pressure insole, and wherein the control system may be configured to generate wearer data based on (i) the related camera signal and (ii) a pressure insole signal from the pressure insole.

In embodiments, the pressure insole may be located within the footwear, ideally in the insole of the footwear. The pressure insoles may be powered by the electrical power source and may be directed by the control system to generate wearer data. Pressure insoles may utilize one or more pressure sensors to assess load distribution during locomotion. These measurements may provide information on gait, ankle function and other functional activity of the lower extremity of the body. In further embodiments, the system may be configured to perform anthropometric measurements such as length, weight, BMI, fat percentage.

In further embodiments, the system may be configured to provide an alert when there is a risk of falling. In yet further embodiments, the system may be configured to provide an alert when there is a risk of muscle, tendon, or ligament injury. The alert may in specific embodiments comprise one or more of sound generation, vibration generation, and light generation.

The control system may be configured to generate the wearer data based on (a) the related camera signal and (b) an inertial measure unit sensor signal of an inertial measure unit sensor which may be functionally coupled to the user wearing the body wearable unit.

In embodiments, the inertial measure units may be wirelessly connected to the remote control system. In embodiments, the inertial measure units may be connected by means of wires to the local control system. The one or more inertial measure units and the pressure insoles may augment the sensor signal information by providing position, movement, force, and torque related information which may be correlated to the image data generated by the camera by means of an artificial neural network. In embodiments, the control system may have a data acquisition software which synchronizes the streams of generated wearer data from one or more cameras, and one or more inertial measure units or pressure insoles or a combination thereof.

The system may comprise an artificial neural network. In embodiments, the artificial neural network may have an artificial neural network architecture selected from the group of a multilayer feed forward network architecture, a single-layer feed-forward network, a single node with its own feedback, single-layer recurrent network, and a multilayer recurrent network.

The artificial neural network may further comprise one or more hidden layers. Each hidden layers may comprise of one or more nodes. The artificial neural network may be configured to assign weights to nodes of the hidden layers in the artificial neural network. The weights may be calculated from the related camera signal and a training mode signal of a training mode sensor using a backpropagation algorithm.

In embodiments, the system may comprise an artificial neural network which may further comprise connections arranged in various layers. In yet further embodiments, the layers may further comprise one or more nodes, which have an associated weight. The choice of number of layers to be used and the number of nodes in each layer is subjective to the particular type of wearer data required. In further embodiments, the artificial neural network may comprise an input layer to receive the external data in the form of sensor signal information, an output layer which generates wearer data (which gives the resultant information about posture, movement, forces and torques), and one or more hidden layer which are intermediate layers between the input and output layer. In embodiments, the artificial neural network may use training algorithms to modify the weights associated with the nodes in each layer, depending on an error rate between generated output and target output.

The input values to the artificial neural network may be multiplied by their corresponding weight and aggregated using a vector to scalar function such as summation, averaging, input maximum, or mode value to produce a single input value. A transfer function may be used to process the calculated input value to produce its output. The processed output is the input signals for the next hidden layer. Typical transfer functions may include sigmoids, hyperbolic-tangents, or other nonlinear functions. This process is repeated across the hidden layers to obtain final output values.

The weights associated with each node, together with the connection pattern determine the signal propagation through the network. They are real numbers (may be positive or negative) that determine the strength of the connectivity between the two connections in the network. Each signal is multiplied by the associated connection weight as the signal is transported through the connection. The input-output relation of the network is a function of the distribution of weights over the connections in the network and are vital to its functioning. Therefore, they may be considered as the distributed knowledge content of the network. The distribution of weights may be determined in a training phase.

In embodiments, the artificial neural network may comprise a convolutional neural network, which may be particularly suited to processing or analyzing image data. In a convolutional neural network, the hidden layers include layers that perform convolutions, where convolution is a mathematical operation on two functions that produces a third function that expresses how the shape of one is modified by the other. The term convolution may refer to both the result function and to the process of computing it. Convolutional neural networks may be ideal for data with a grid-like topology (such as images) as spatial relations between separate features may be taken into account during convolution.

The artificial neural network may be calibrated by means of the training mode (TM2). The wearer data for calibration may be generated from the related camera signal and a training mode signal of a training mode sensor. The artificial neural network may in embodiments then be trained using wearer data generated by assuming a predetermined routine of postures and movement.

In embodiments, the training mode sensors may comprise one or more of inertial measure units, pressure insoles or a combination thereof. In embodiments, the training mode may comprise using a backpropagation algorithm to train the artificial neural network. First, the artificial neural network may be provided with training mode signal as input from the one or more cameras, or one or more training sensors, or a combination thereof. Next, the outputs from the network, which may be the movement, posture, force, and torque information are computed. The actual movement, posture, force, and torque information may be measured by one or more inertial measure units or pressure insoles or a combination thereof. The error between the output computed by the neural network and the measured information is then calculated. The backpropagation algorithm starts with random weights and adjusts these weights in a manner that reduces this error until a required level of accuracy is achieved. The training of the artificial neural network may involve identifying the correct combination of weights associated with each node that minimizes this error.

The control system may be configured to execute (i) a first training mode (TM2) and (ii) a controlling mode (CM). During execution of the training mode (TM2), the control system may be trained based on the related camera signal and a training mode signal of a training mode sensor generated during the training mode (TM2), to provide a trained control system. During execution of the control mode (CM) the trained control system may be configured to generate the wearer data based on the related camera signal generated during control mode (CM).

In embodiments, the control system may be configured with a base algorithm which facilitates the training of the artificial neural network. The training of the artificial neural network may be vital to generating optimal wearer data for a specific activity or exercise. In embodiments, the neural network may be trained in two stages, a basic controller training stage and the first training mode stage. In the controller training, the convolutional artificial neural network may undergo supervised learning, where inertial measure units, pressures insoles, optical motion capture system, manual measurements or other posture detection technology may be used to train the artificial neural network to generate wearer data from related camera signals. This may be a computationally expensive process requiring several hundred to thousand computer hours of external processing.

In embodiments, the control system may be configured to execute the first training mode after the basic controller training. The first training mode may calibrate the system uniquely to the wearer and trains the artificial neural network to uniquely generate wearer data for a specific activity or exercise. In embodiments, this stage may involve, first, the user wearing the training mode sensors at the required positions on their limbs. Next, the user may perform a predetermined routine of postures and movements. For example, a person playing basketball may have to perform the routine exercise of shooting, dribbling and maintain a defensive posture to first, further train the artificial neural network to interpret these specific motions and second, to calibrate the sensors and output wearer data to the specific athlete. In this example, the basic controller training may have a general system calibrated to an individual of average height and weight, configured for basic activities such as walking or running. Now, the control system is trained, and the system may be capable of determining information such as posture, movement, force, and torque from wearer data solely from one or more cameras, without the use of additional sensors. In embodiments, the first training mode may be executed in the absence of training mode sensors, where the artificial neural network may be trained using an unsupervised or a reinforcement learning technique. The execution of the first training mode or control mode of the system may be executed on rudimentary processors, for example a Raspberry-pi.

In embodiments, the system may have the feature to select from a number of basic controller training options, which may be made available from a centralized database via remote control system. This provides the benefit of updating the basic controller training remotely for new body types and for a multitude of new sport or motion capture or physical therapy activities.

In embodiments, the control system may determine the mode of operation of the system. In the control mode of operation of the system, the wearer may be able to generate wearer data relating to movement and posture in the absence of training mode sensors. The trained system operating in the control mode may provide wearer data from which it may be possible to extract position, load, and acceleration information in relation to the movement of limbs. From this information, the system may compute kinetic information about muscle states, joint torques, joint motion, muscle excitation, and neuro activation. In embodiments, the system may change the mode of training to be suitable for different activities. The position at which the training sensors are placed may be altered to train the control system to be trained for different activities in the training mode.

In embodiments, the control mode may be executed simultaneously with the first training mode. The wearer data generated during the control mode may be used to further train the artificial neural network.

In a further aspect, the invention provides a kit of parts. In embodiments, the kit of parts may comprise (i) the system (comprising the body wearable unit, such as footwear) as described herein, and (ii) a manual. Especially, the kit of parts may comprise (i) the body wearable unit, such as footwear, as described herein, and (ii) a manual. Especially, the manual may comprise instructions for a user to use the body wearable unit for training the control system. The manual may describe a routine for a series of postures or movements related to a number of popular activities or exercises to calibrate the system to an individual doing a specific activity. For example, the routine may comprise a series of walking exercises to calibrate the response of the system to gait, a series of lunges, and squats to calibrate the system to the lower extremity of the body. In further embodiments, there may be specific routines tailored to specific exercises or activity sets.

In embodiments, the manual may describe field tests to assess physical performance such as jump tests (i.e. counter movement jump) for strength, sprint tests over different distances (i.e., 10 m and 30 m) for speed, and interval shuttle run test (ISRT) for intermittent endurance. With these tests, individual responses to training and rehabilitation may be assessed for strength, speed, and endurance.

In further embodiments, the manual may describe tests to assess whether physical and psychosocial load influences performance, these tests may be developed specifically for team sports. Physical performance tests that may often be used are jump tests or the one repetition maximum test (e.g., CMJ, SJ, or 1RM) for strength, sprint tests over different distances (i.e., 5 m, 10 m, 20 m, and 40 m) for speed, and Yo-Yo intermittent recovery tests for endurance. With these tests, individual responses to training may be assessed for strength, speed, and endurance.

Hence, the herein indicated wearer data may also be selected from strength, speed, and endurance.

In yet further embodiments, the manual may be made available digitally, accessible via the internet, where the manual may be periodically updated to include additional routines for specific activities or sports. The term "manual" may refer to a physical manual but may also refer to a reference to a manual, such as a QR code or other code to guide a user to a manual on the internet.

In a further aspect, the invention may provide a method for generating wearer data using the system described before. The method may comprise first, monitoring with one or more cameras a user wearing the body wearable unit and providing a related camera signal, and second, generating wearer data based on the related camera signal, wherein the wearer data may comprise one or more of (i) wearer posture related data and (ii) wearer movement related data.

In embodiments, the method may describe the use of the system where the camera signal from the one or more cameras is provided to the control system, which may process the data by means of a trained artificial neural network. The artificial neural network from the related camera signal or sensor signal or a combination thereof, may first determine the location of different limbs and segments of the body, which allows it to identify the location of joints. From motion data, the artificial neural network may then identify the acceleration of the different appendages connected to the joints. In embodiments, the method of inverse kinematics or inverse dynamics or a combination thereof may be employed to generate wearer data such as body postures, joint angles, joint loads, muscle usage and loads, and feet contacting forces. Inverse kinematics and inverse dynamics are the mathematical process of calculating the variable joint parameters needed to place the end of a kinematic chain, such as a wearer's limb or appendage, in a given position and orientation relative to the start of the chain. The muscle states may be calculated based on the real-time simulation of the neural-musculoskeletal model of the user, using the decomposed body movement and stepping forces.

In embodiments, the method described may utilize a training mode sensor which comprises the inertial measure unit sensor.

In embodiments, training mode sensor may comprise a global positioning sensor (GPS) and heart rate sensors, which may allow load (both internal and external) to be measured with GPS, FITT principle (Frequency, Intensity, training Type, and Time) and heartrate. In yet further embodiments, navigation satellite systems such as the BeiDou Navigation Satellite System (BDS) may be used to determine local position. Physical load may be defined by training programs or exercises and/or by monitoring training and competition loads. This may include both external (frequency, intensity, time/duration, and training type) as internal load (heart rate, rate of perceived exertion, etc.) measures. Psychosocial load may be defined as, for example, daily hassles, negative life events, and stress levels. Physical performance of the lower extremity may be measured in the categories: strength (e.g., countermovement jump), speed (e.g., sprint times) and endurance (Yo-Yo Intermittent Recovery test (Yo-Yo IRT)) measures.

In further embodiments, additional indirect measurements such as training impulse, acute chronic workload ratio, monotony and strain may be generated as wearer data.

In further embodiments, the system may be configured to generate information related to agility as wearer data, while a soccer player performs a T-test.

In embodiments, the system may be configured to provide a digital model scaled to the base body height and weight as wearer data, based on joint angles, user entered body weight and height. In this embodiment, the digital model may contain the mass inertial properties of each body segment. Further, it may also contain muscle models to estimate the muscle usage and loads.

In embodiments, the method described may comprise retrieving a pressure insole signal from the pressure insole, and generating wearer data based on (i) the related camera signal and (ii) the pressure insole signal.

In embodiments the method may further comprise retrieving an inertial measure unit sensor signal of an inertial measure unit sensor functionally coupled to the user wearing the body wearable unit, such as footwear, and generating wearer data based on (i) the related camera signal and (ii) the inertial measure unit sensor signal.

In embodiments, the method may further comprise executing a first training mode (TM2) and a controlling mode (CM). The training mode (TM2) may comprise training the control system based on the related camera signal and a training mode signal of a training mode sensor generated during the training mode (TM2), to provide a trained control system. The control mode (CM) may comprise generating with the trained control system the wearer data based on the related camera signal generated during control mode (CM).

The method may describe acquiring wearer data, which may additionally comprise a related training mode sensor signal which may further comprise a signal from one or more inertial measure units or pressure insoles or a combination thereof. The method may describe the use of these signals in first, a training mode to train the control system, and second, use the trained control system in a control mode, where wearer data may be generated from one or more related camera signals.

In embodiments, the first training mode may utilize supervised learning, which is a tool used to train the artificial neural network to yield the desired output. The training may involve correlating the posture information that is obtained from the related camera signal with the measured position and movement information obtained from the training sensor signal. In embodiments, a back propagation algorithm may be used to adjust the weights associated with the hidden layers in the artificial neural network until the error has been sufficiently minimized i.e. training sensor data may be estimated from solely the related camera signal. In embodiments, the control system may then use the method of inverse kinematics or inverse dynamics or a combination thereof to generate wearer data such as body postures, joint angles, joint loads, muscle usage and loads, and feet contacting forces.

In embodiments, the first training mode may utilize unsupervised learning which may use the related camera signal in the absence of training sensor signals. This is particularly useful when there is a necessity to record a type of body motion or posture that is not directly inferable from training mode sensors. In embodiments, unsupervised learning algorithms may be selected from the group of a hierarchical, a k-means, or a Gaussian mixture model. In embodiments, the first training method may utilize semi-supervised learning, which occurs when only part of the camera signal is provided in conjunction with related training sensor signal. This may be the training method employed when the first training mode and the control mode are executed simultaneously. In embodiments, the first training method may utilize reinforcement learning, which is advantageous in operating the system in the absence of training sensor signals. Especially, the method may focus on finding a balance between generating wearer data using information solely from camera signal and reference data of related activity or exercise in a centralized database. In embodiments, partially supervised reinforcement learning algorithms may be used which combine the advantages of supervised and reinforcement learning algorithms.

In embodiments, the method may further comprise retrieving information from a remote control system and generating wearer data based on (i) the related camera signal and (ii) the information from the remote control system.

The user may by means of the remote control system direct the local control system to operate in one of the training mode or control mode. This may be facilitated by the communication system which may allow communication between the remote control system and local control system, which may enable the user to modify the mode of operation of the system remotely. In further embodiments, the remote control system may be used to toggle the different data streams in the wearer data. In further embodiments, the user by means of the remote control system may configure alternative training modes for different activities.

In embodiments, the training of the control system to generate wearer data may involve communicating with a centralized database, which may be facilitated by means of the remote control system.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 2, schematically depicts a remote control system 320;

FIG. 3 schematically depicts an athlete wearing the system 1, with inertial measure units 610 distributed over the different segments of his body and a body wearable unit 1000 with a first camera 210 on either shoe;

FIG. 4 schematically depicts a sole part;

DETAILED DESCRIPTION OF THE EMBODIMENTS

Figure 1:
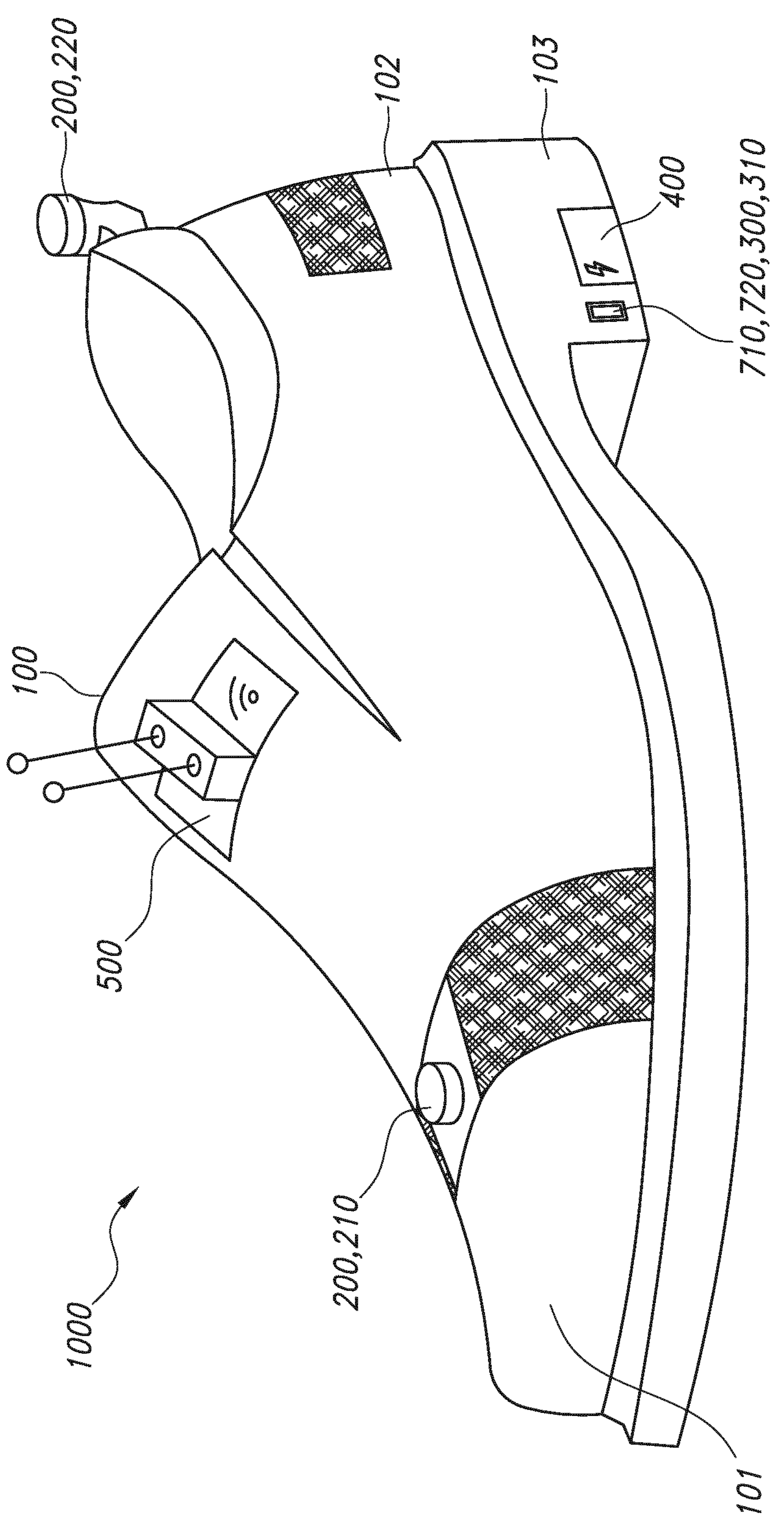
FIG. 1 schematically depicts the body wearable unit 1000.

FIG. 1 schematically depicts a system 1 which may comprise a body wearable unit 1000, with one or more cameras 200, a control system 300, and an electrical power source 400. The body wearable unit 1000 may comprise the one or more cameras 200, the control system 300, and the electrical power source 400. The one or more cameras 200 may be configured to monitor a user wearing the wearable unit and may be used to provide a related camera signal. The electrical power source 400 may be configured to provide electrical power to the one or more cameras 200, and the control system 300. The control system 300 may be configured to generate wearer data based on the related camera signal. The wearer data may comprise one or more of (i) wearer posture related data and (ii) wearer movement related data. The body wearable unit 1000 may comprise footwear and the one or more cameras 200, the control system 300, and the electrical power source 400 which may be functionally coupled to the body wearable unit 1000. The footwear may comprise a front part 101; wherein the one or more cameras 200 may comprise a first camera 210, wherein the first camera 200 is physically coupled to the front part 101 of the footwear. The footwear may comprise a back part 102, wherein the one or more cameras 200 may comprise a second camera 220, wherein the second camera 220 may be physically coupled to the back part 102 of the footwear 100.

In this specific embodiment, the system may be a body wearable unit 1000 that may comprise a front camera 210 secured to the front part of the shoe 101, a second camera secured to the back part of the shoe 102, a control system 300 and an electrical power source 400 housed in the sole 103 of the shoe. The front camera 210 and back camera 220 record the anterior and posterior of the wearer, respectively. The two cameras 210, 220 may be electrically powered by the electrical power source 400 by means of wires (not visible) stitched between the layers of the shoe.

The body wearable unit 1000 may further comprise a communication system 500, wherein the electrical power source 400 may be configured to provide electrical power to the communication system 500, and wherein the communication system 500 may be functionally coupled to the body wearable unit, such as the footwear 100. The communication system 500 may be configured to provide the wearer data to a receiver 510 external of the body wearable unit 1000. In the specific embodiment depicted in FIG. 1, the communication system may contain flaps that are stitched onto the front of the shoe i.e., to the tongue of the shoe. The communication system depicted here may have tiny antennae to transmit data to an external receiver via Wi-Fi. The communication unit may be powered using wires connected to the electrical power source 400. The wires (not visible) may be stitched between the layers of the shoe.

The control system 300 may comprise a local control system 310 and a remote control system 320. The electrical power source 400 may be configured to provide electrical power to the local control system 310. The local control system 310 may be functionally coupled to the body wearable unit, such as the footwear 100. The communication system 500 may be configured to communicate between the local control system 310 and the remote control system 320. The control system 300 may be configured to generate wearer data based on (i) the related camera signal and (ii) information from the remote control system 320.

In this specific embodiment, control system may consist of the local control system 310 and the remote control system 320, where the local control system 310 may be placed in a cavity in the sole 103 of the shoe. It may receive power from the electrical power source 400 located close to it, also in the sole part 103 of the shoe. It may connected by wires (not visible) stitched between the layers of the shoe to the communication system 500, the first camera 210 and the second camera 220. The local control system 310 may be in communication with the remote control system 320 via the communication system 500. The remote control system 320 may be used to change the parameters under which the first camera 210 or the second camera 220 operate. It may be used to regulate the electrical power source 400. Further, the remote control system 320 may be used to patch or update the software installed on the local control system 310. The local control system 310 may be configured to process the data from the one or more cameras 200 and generate wearer data, which may be transmitted to the remote control system 320. The embodiment may also be configured to transmit the related camera signals from the one or more cameras 200 to the remote control system 320 by means of the communication system 500. Which may provide the benefit of processing the data externally.

FIG. 2 schematically depicts an external or remote control system 320, which may comprise a communication system 510. In this embodiment depicted in FIG. 2, the communication system may facilitate communication between the local control system 310 and the remote control system 320. The remote control system 320 may have some buttons to quickly change the mode of operation of the system 1 or a part of it. The local control system 310 may also be configured to wirelessly transmit the received wearer data or a camera signal or a sensor signal to another control system, for example a computer.

FIG. 3 schematically depicts a system 1 that may comprise the inertial measure unit sensor 610. The inertial measure unit sensor 610 may be configured external of the footwear 100. The inertial measure unit 610 may comprise one or more of a gyroscope, an accelerometer, and a magnetometer.

In the specific embodiment depicted in FIG. 3, the wearer may be wearing several inertial measure units 610 on the different segments of his or her body including the torso, the arms, and the legs. The inertial measure units may be attached to the different appendages of the wearer by means of Velcro straps that may be tightly fastened to the different segments of the body. The inertial measure units may be powered by a local battery located within the inertial measure units. These units may also host Wi-Fi modules which facilitate the transfer of information to the communication system 500. In this embodiment, the inertial measure units may comprise a GPS and an accelerometer. The accelerometer may provide information about the movement of each of the inertial measure units, which by extension indicates the acceleration of each of the different segments of the wearers body. The GPS may be used to identify changes in orientation and position, and hence posture related information may be measured. These sensors generate information related to posture and movement during the course of an activity or an exercise, and this information may be transmitted wirelessly to the communication system 500. The sensors may be used only when the first training mode (TM2) is activated. The communication system may direct this data to the control system 300 if the system is used in the first training mode. When the first training mode is activated, the sensor signal from the inertial measure units 610 in combination with the related camera signals from the one or more cameras 200 may be processed in the control system 300.

The control system 300 may be configured to generate the wearer data based on (a) the related camera signal and (b) an inertial measure unit sensor signal of an inertial measure unit sensor 610 functionally coupled to the user wearing the wearable unit. The artificial neural network 710 may be calibrated by means of the training mode (TM2), wherein one or more of the following may apply: (a) wearer data for calibration may be generated from the related camera signal and a training mode signal of a training mode sensor 620 and (b) wearer data may be generated by assuming a predetermined routine of postures and movement. A kit of parts which may comprise a manual 901, which may further comprise instructions for a user to use the body wearable unit 1000 for training the control system 300 is provided.

The specific embodiment depicted in FIG. 3, may comprise an artificial neural network 710 that may have already undergone controller training externally, prior to the use of the system 1. The wearer may adorn the different sensors in the different indicated segments of their body and may activate the first training mode (TM2). For example, for the wearer to practice kickboxing, the manual may detail a series of basic movement routines followed by a series of different kicks. The wearer may perform these routines while wearing the body wearable unit 1000 in addition to the inertial measure units 610, 620. This may enable the system 1 to first calibrate to the user and second to the specific activity i.e., kickboxing. In another specific embodiment, an ice-skating athlete may perform tests using the system 1 such as jump tests, Wingate test, VO2-max test, recovery test and breathing test. In this embodiment, the system 1 may be configured to generate test results as wearer data. The system 1 may use information regarding velocity, angles, torques, and forces on muscles. In yet another specific embodiment, the system may comprise an immersible and waterproof footwear to generate swimming related wearer data such as strokes per meter, number of strokes, diving angles, meters under water, aerodynamics, pacing behavior.

The control system 300 may be configured to execute a first training mode (TM2) and a controlling mode (CM). During execution of the training mode (TM2) the control system 300 may be trained based on the related camera signal and a training mode signal of a training mode sensor 620 generated during the training mode (TM2), to provide a trained control system 300. During execution of the control mode (CM) the trained control system 300 may be configured to generate the wearer data based on the related camera signal generated during control mode (CM). The wearer data may comprise information about one or more of load capacity, kicking force, etc.

In this specific embodiment, upon successful calibration of the system 1 by means of enabling the first training mode (TM2), the system is now calibrated to the specific activity of interest and to the specific user. Now, the wearer may enable the control mode (CM), which may generate data solely from the camera signal. In this embodiment, the artificial neural network 710 may process the camera signal to identify position and acceleration of the limbs. Further, it may process the image to identify the position of the different joints as well as the orientation of the different limbs. This information may be used by the control system 300 to estimate the joint angles and muscle state, by means of inverse kinematics or inverse dynamics or a combination thereof. This information may be further processed to estimate information such as load capacity on joints and kicking force. In other embodiments, in the system 1 depicted in FIG. 3, the first training mode may also be enabled in addition to the control mode (CM). In this setting, the system 1 may generate additional information that may help further train the artificial neural network 710 while it continues to generate wearer data as a result of the control mode (CM) also being enabled. In this specific embodiment, it may not be necessary that the inertial measure units 610 are placed on the body of the wearer i.e. when only the control mode is enabled. In other embodiments, it may be possible to enable the first training mode (TM2) and the control mode (CM) even in the absence of the inertial measure units. This is possible as the artificial neural network 710 may also use unsupervised learning or reinforcement learning algorithms which facilitate this.

FIG. 4 schematically depicts the system 1 where the footwear 100 may comprise a sole part 103, wherein the sole part 103 comprises one or more of (i) at least part of the control system 300 and (ii) the electrical power source 400. The sole part 103 may comprise the local control system 310.

In the specific embodiment depicted in FIG. 4, the sole part 103 of the shoe may comprise cavities that are specifically shaped to the outline of the components they intend to house. In this specific embodiment, the electrical power supply 400 and the local control system 310 may be placed in the sole part 103 of the shoe. The rubber material of the modern shoe cushions these components from vibrations and contact with the external environment. Further, they may also isolate the user from coming into physical contact with these electrical components. In other embodiments, the communication system 500 may also be housed within the sole part 103 of the shoe.

The footwear 100 may further comprise a pressure insole 630, wherein the pressure insole 630 may be functionally coupled to the body wearable unit 1000, wherein the electrical power source 400 may be configured to provide electrical power to the pressure insole 630, and wherein the control system 300 may be configured to generate wearer data based on (i) the related camera signal and (ii) a pressure insole signal from the pressure insole 630. The pressure insole 630 may comprise one or more pressure sensors.

In the specific embodiment depicted in FIG. 4, pressure insole 630 comprising of multiple pressure sensors may be stitched into the insole of the shoe. These may be powered by means of wires (not visible) routed through the underlining of the shoe to the electrical power supply 400. The wires for the transfer of data may also be routed in a similar manner to the control system 300. The control system 300 may use this data in combination with the one or more camera signals to train the artificial neural network 710, when the first training mode (TM2) is enabled.

Figure 5:
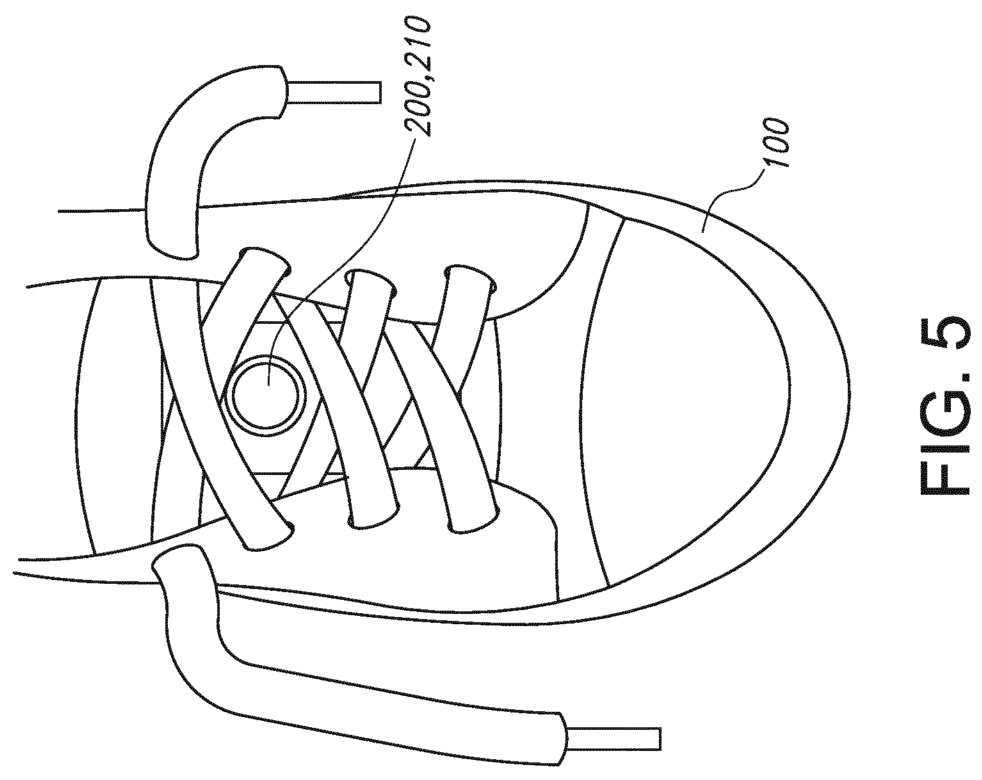
FIG. 5 schematically depicts an embodiment of the system 1 with a first camera 210 secured using laces.

FIG. 5 schematically depicts the system 1 where the first camera 210 may be physically coupled to the front part 101 of the footwear 100 by means of one or more of (a) a shoelace, (b) a stitched cavity, (c) a Velcro strap connection, and (d) a camera holder element fastened below or between a shoelace or Velcro strap.

In this specific embodiment, which depicts a sports shoe such as a sneaker, where the first camera 210 may be physically secured in place by means of shoelaces. The first camera 210 here, may possess fabric flaps that sit flush on the tongue of the shoe upper. The laces may be fastened over the first camera 210 without occluding the field of view of the first camera 210.

Figure 6:
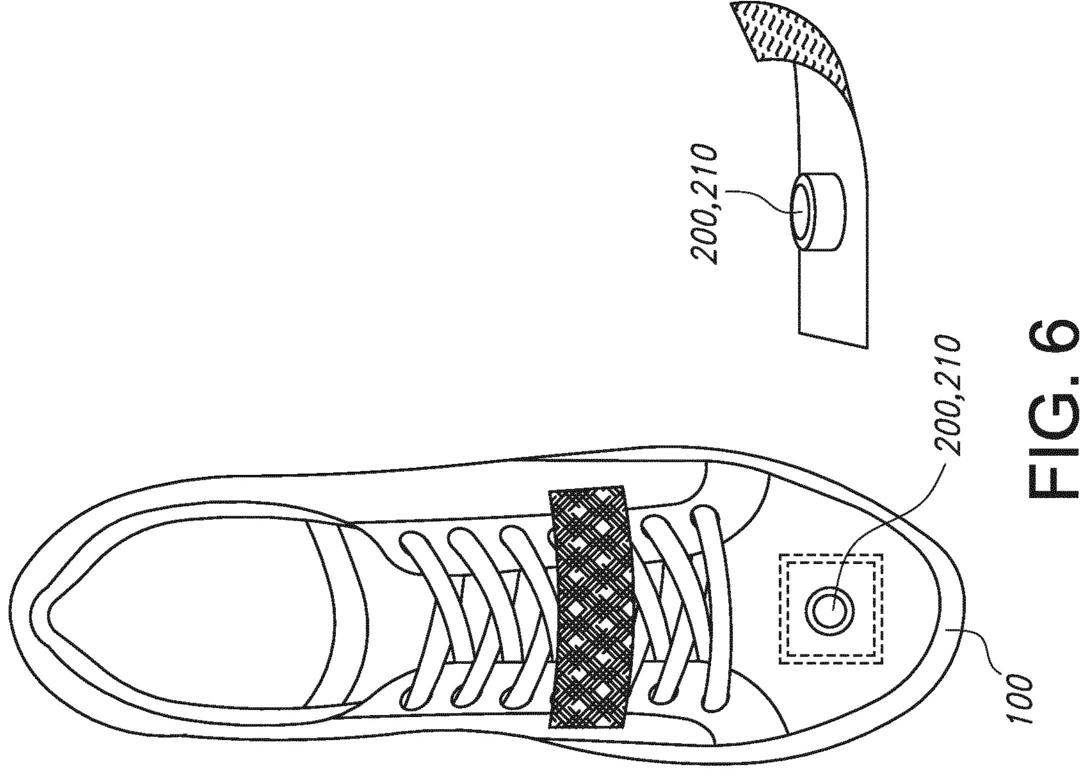
FIG. 6 schematically depicts an embodiment of the system 1 with two first cameras 210 secured to the front part 101 of the shoe.

FIG. 6 schematically depicts an embodiment which may comprise 2 first cameras 210 where one of the first camera 210 may be secured to the toe-box of the shoe by means of a stitched cavity. This may comprise a cavity that may be used to house the shoe. A cloth or fabric cover with an opening to allow unrestricted field of view of the first camera 210 may be placed over the cavity. The cloth may then be stitched onto the toe-box of the shoe securing the first camera 210 in place.

The second camera 220 may be physically coupled to the back part 102 of the footwear 100 by means of one or more of (a) a stitched cavity, (b) a Velcro strap connection, and (c) a camera holder element fastened below or between a Velcro strap.

One or more of the one or more cameras 200 may be selected from the group of an optical camera, an infrared camera, a multispectral camera, and a LIDAR sensor.

Figure 7:
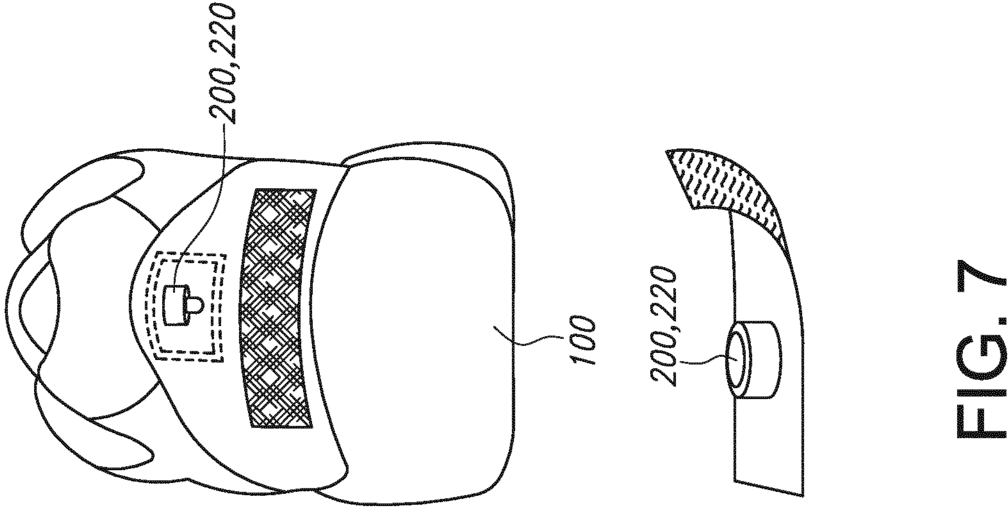
FIG. 7 schematically depicts an embodiment of the system 1 with two second cameras 220 secured to the back part 102 of the shoe.

FIG. 7 schematically depicts a specific embodiment which may be a sports shoe comprising two second cameras 220 attached to the back part 102 of the shoe. One of the second cameras may be attached close to the topline of the shoe by means of a camera holder. The camera holder may be stitched to the back of the shoe and may be secured in place. The second camera may then be attached to the holder and secured in place. In this embodiment, the camera may be directed vertically upwards to capture the posterior of the wearer in the field of view of the second camera. The camera holder may provide greater flexibility in orienting the camera. Another second camera 220 may be attached to the bottom of the back part 102 of the shoe above the sole part 103 of the shoe. This second camera 220 may be attached to the back of the shoe by means of a Velcro strap, which may allow the camera on the male part of the Velcro strap to be strapped into the female part of the Velcro strap in the back part of the shoe.

Figure 8:
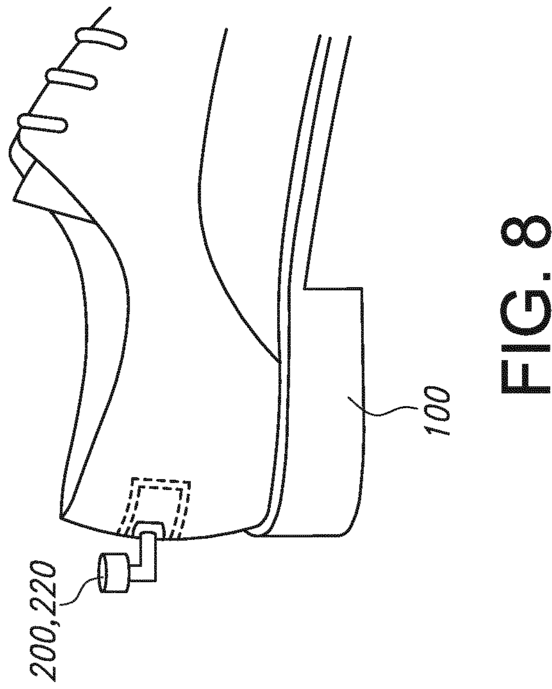
FIG. 8 schematically depicts an embodiment of the system 1 with a second cameras 220 secured to the back part 102 of the shoe by means of a camera holder.

FIG. 8 schematically depicts a specific embodiment of the system 1, where a second camera 220 may be attached to the back part 102 of the shoe close to the shoe topline by means of a holder. The holder may be stitched onto the shoe and may have a mount that secures the second camera 220 in place.

Figure 9:
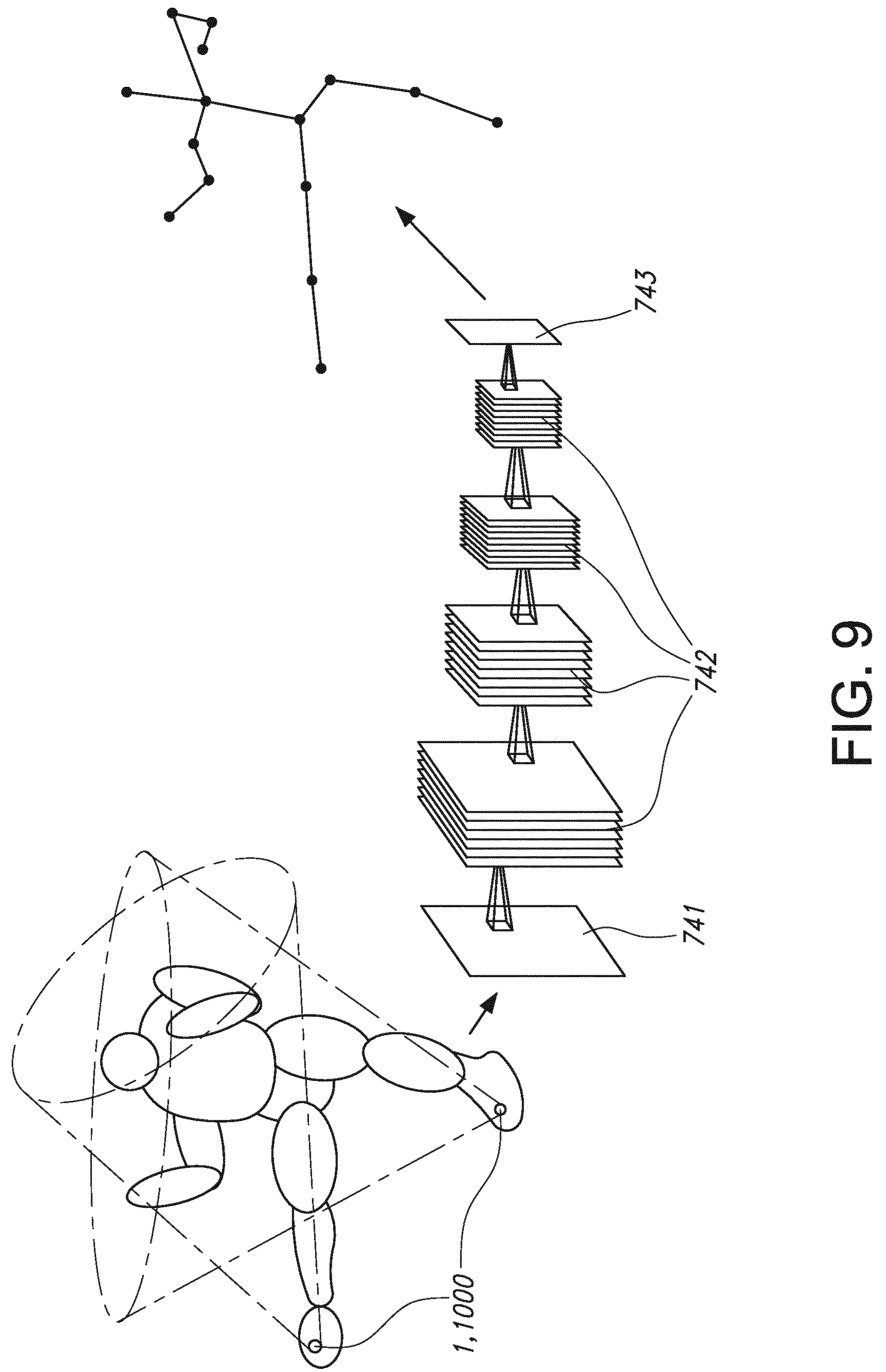
FIG. 9 schematically depicts an embodiment of the artificial neural network 710 which may be used by the system 1. The schematic drawings are not necessarily to scale.

FIG. 9 schematically depicts a visualization of an embodiment of the artificial neural network 710. The layers on depicted on the left side may comprise the series of images or image data from related camera signal that are the inputs to the input layer 741. Each of the subsequent layers in the middle may be the hidden layers 742. The hidden layers may comprise a number of nodes, each with an associated weight. The input from each layer undergoes a convolution and is transferred to the subsequent layer. The last layer on the right may comprise the output layer 743 which outputs the required wearer data. In the specific embodiment depicted in FIG. 9, the user performs a series of kicks which may be recorded by the two camera, to provide related camera signals as input to the input layer 741. The artificial neural network in this specific embodiment has 4 hidden layers 742, which perform a series of convolutions to generate an output at the output layer 743. The output in this embodiment may be a biomechanical model with information on the position and movement of the different segments of the body.

The term "plurality" refers to two or more. The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%. The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage. In yet a further aspect, the invention (thus) provides a software product, which, when running on a computer is capable of bringing about (one or more embodiments of) the method as described herein.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

Hence, amongst others, the invention provides a system comprising a body wearable unit, with one or more cameras, a control system, and an electrical power source. The invention further provides a method for generating wearer data using the system, wherein the method comprises monitoring with one or more cameras a user wearing the wearable unit and providing a related camera signal; generating wearer data based on the related camera signal, wherein the wearer data comprise one or more of (i) wearer posture related data and (ii) wearer movement related data.

The invention claimed is:

1. A system comprising a body wearable unit, one or more cameras, a control system, and an electrical power source; wherein:

the body wearable unit comprises the one or more cameras, the control system, and the electrical power source;

the one or more cameras are configured to monitor a user wearing the wearable unit and to provide a related camera signal, wherein the one or more cameras are configured to record a body of the user, the one or more cameras looking upwards from a lower extremity;

the electrical power source is configured to provide electrical power to the one or more cameras, and the control system;

the control system is configured to generate wearer data based on the related camera signal; wherein the wearer data comprises (i) wearer posture related data and (ii) wearer movement related data;

the body wearable unit comprises footwear, wherein the footwear comprises a shoe or a boot; and the one or more cameras, the control system, and the electrical power source are functionally coupled to the body wearable unit.

2. The system according to claim 1, wherein the body wearable unit further comprises a communication system, wherein the electrical power source is configured to provide electrical power to the communication system, and wherein the communication system is functionally coupled to the body wearable unit.

3. The system according to claim 2, wherein the communication system is configured to provide the wearer data to a receiver external of the body wearable unit.

4. The system according to claim 2, wherein the control system comprises a local control system and a remote control system, wherein the electrical power source is configured to provide electrical power to the local control system, wherein the local control system is functionally coupled to the body wearable unit; wherein the communication system is configured to communicate between the local control system and the remote control system; wherein the control system is configured to generate wearer data based on (i) the related camera signal and (ii) information from the remote control system.

5. The system according to claim 1, wherein the footwear comprises a front part; wherein the one or more cameras comprise a first camera, wherein the first camera is physically coupled to the front part of the footwear.

6. The system according to claim 5, wherein the first camera is physically coupled to the front part of the footwear by means of one or more of (a) a shoelace, (b) a stitched cavity, (c) a Velcro strap connection, and (d) a camera holder element fastened below or between a shoelace or Velcro strap.

7. The system according to claim 1, wherein the footwear comprises a back part, wherein the one or more cameras comprise a second camera, wherein the second camera is physically coupled to the back part of the footwear.

8. The system according to claim 7, wherein the second camera is physically coupled to the back part of the footwear by means of one or more of (a) a stitched cavity, (b) a Velcro strap connection, and (c) a camera holder element fastened below or between a Velcro strap.

9. The system according to claim 1, wherein the footwear comprises a sole part, wherein the sole part comprises one or more of (i) at least part of the control system and (ii) the electrical power source.

10. The system according to claim 4, wherein the footwear comprises a sole part, wherein the sole part comprises one or more of (i) at least part of the control system and (ii) the electrical power source, and wherein the sole part comprises the local control system; and wherein the sole part comprises the electrical power source.

11. The system according to claim 1, wherein the control system is configured to generate the wearer data based on (a) the related camera signal and (b) an inertial measure unit sensor signal of an inertial measure unit sensor functionally coupled to the user wearing the wearable unit.

12. The system according to claim 11, wherein the system comprises the inertial measure unit sensor; wherein the inertial measure unit sensor is configured external of the footwear.

13. The system according to claim 11, wherein the inertial measure unit comprises one or more of a gyroscope, an accelerometer, and a magnetometer.

14. The system according to claim 1, wherein the system comprises an artificial neural network having an artificial neural network architecture selected from the group consisting of a multilayer feed forward network architecture, a single-layer feed-forward network, a single node with its own feedback, single-layer recurrent network, and a multilayer recurrent network.

15. The system according claim 14, wherein the artificial neural network comprises one or more hidden layers, wherein each hidden layer comprises of one or more nodes, wherein: (a) the artificial neural network is configured to assign weights to nodes of the hidden layers in the artificial neural network, and/or (b) the weights are calculated from the related camera signal and a training mode signal of a training mode sensor using a backpropagation algorithm.

16. The system according to claim 1, wherein the control system is configured to execute a first training mode (TM2) and a controlling mode (CM), wherein: (i) during execution of the training mode (TM2) the control system is trained based on the related camera signal and a training mode signal of a training mode sensor generated during the training mode (TM2), to provide a trained control system; and (ii) during execution of the control mode (CM) the trained control system is configured to generate the wearer data based on the related camera signal generated during control mode (CM).

17. The system according to claim 16, wherein the training mode signal comprises an inertial measure unit sensor signal.

18. The system according to claim 14, wherein the artificial neural network is calibrated by means of a training mode (TM2), wherein one or more of the following applies: (i) wearer data for calibration are generated from the related camera signal and a training mode signal of a training mode sensor, and (ii) wherein wearer data are generated by assuming a predetermined routine of postures and movement applies.

19. The system according to claim 1, wherein the wearer data comprise information about one or more of load capacity, kicking force, muscle state, muscle force, muscle torques and/or joint loads.

20. The system according to claim 1, wherein the footwear further comprises a pressure insole, wherein the pressure insole is functionally coupled to the body wearable unit, wherein the electrical power source is configured to provide electrical power to the pressure insole, and wherein the control system is configured to generate wearer data based on (i) the related camera signal and (ii) a pressure insole signal from the pressure insole.

21. The system according to claim 20, wherein the pressure insole comprises a pressure sensor.

22. The system according to claim 1, wherein one or more of the one or more cameras are selected from the group consisting of an optical camera, an infrared camera, a multispectral camera, and a LIDAR sensor.

23. The system according to claim 1, wherein the footwear comprises a sports shoe selected from the group consisting of soccer shoes, running shoes, and skates.

24. A method for generating wearer data using the system according to claim 1, wherein the method comprises: (a) monitoring with one or more cameras a user wearing the wearable unit and providing a related camera signal, wherein the one or more cameras are configured to record a body of the user, the one or more cameras looking upwards from a lower extremity; and (b) generating wearer data based on the related camera signal, wherein the wearer data comprises (i) wearer posture related data and (ii) wearer movement related data.

25. The method according to claim 24, further comprising retrieving information from a remote control system and generating wearer data based on (i) the related camera signal and (ii) the information from the remote control system.

26. The method according to claim 24, further comprising retrieving an inertial measure unit sensor signal of an inertial measure unit sensor functionally coupled to the user wearing the wearable unit and generating wearer data based on (i) the related camera signal and (ii) the inertial measure unit sensor signal.

27. The method according to claim 24, further comprising executing a first training mode (TM2) and a controlling mode (CM), wherein: (a) the training mode (TM2) comprises training the control system based on the related camera signal and a training mode signal of a training mode sensor generated during the training mode (TM2), to provide a trained control system; and (b) the control mode (CM) comprises generating with the trained control system the wearer data based on the related camera signal generated during control mode (CM).

28. The method according to claim 27, wherein the training mode sensor comprises an inertial measure unit sensor.

29. The method according to claim 24, further comprising retrieving a pressure insole signal from the pressure insole, and generating wearer data based on (i) the related camera signal and (ii) the pressure insole signal.

30. A kit of parts comprising a system according to claim 1 and a manual, wherein the manual comprises instructions for a user to use the body wearable unit for training the control system.

* * * * *